United States Patent [19]
Boone et al.

[11] Patent Number: 5,582,723
[45] Date of Patent: Dec. 10, 1996

[54] CHROMATOGRAPHY CARTRIDGE

[75] Inventors: Ernest L. Boone, Zion; Richard A. Henry, State College, both of Pa.

[73] Assignee: Keystone Scientific, Inc., Bellefonte, Pa.

[21] Appl. No.: 419,523

[22] Filed: Apr. 10, 1995

Related U.S. Application Data

[63] Continuation of Ser. No. 157,469, Nov. 26, 1993, abandoned.

[51] Int. Cl.⁶ .............................................. B01D 15/08
[52] U.S. Cl. ................................. 210/198.2; 210/656
[58] Field of Search ........................... 210/656, 659, 210/198.2, 450; 95/82; 96/101, 105, 106; 422/70

[56] References Cited

U.S. PATENT DOCUMENTS

| | | | |
|---|---|---|---|
| 3,487,938 | 1/1970 | Patterson | 210/198.2 |
| 3,511,377 | 5/1970 | Hrdina | 210/198.2 |
| 3,682,315 | 8/1972 | Haller | 210/198.2 |
| 3,904,527 | 9/1975 | Wilhelmson | 210/198.2 |
| 4,026,803 | 5/1977 | Abrahams | 210/198.2 |
| 4,093,550 | 6/1978 | Stahl | 210/198.2 |
| 4,187,177 | 2/1980 | Stahl | 210/198.2 |
| 4,234,427 | 11/1980 | Boehme | 210/198.2 |
| 4,283,280 | 8/1981 | Brownlee | 210/198.2 |
| 4,313,828 | 2/1982 | Brownlee | 210/198.2 |
| 4,399,032 | 8/1983 | Mott | 210/198.2 |
| 4,451,363 | 5/1984 | Brownlee | 210/198.2 |
| 4,451,364 | 5/1984 | Higgins | 210/198.2 |
| 4,451,365 | 5/1984 | Sattler | 210/198.2 |
| 4,551,249 | 11/1985 | Shackelford | 210/198.2 |
| 4,655,917 | 4/1987 | Shackelford | 210/198.2 |
| 4,670,141 | 6/1987 | Shackelford | 210/198.2 |
| 4,732,672 | 3/1988 | Kiang | 210/198.2 |
| 4,732,687 | 3/1988 | Muller | 210/198.2 |
| 4,737,284 | 4/1988 | Hauke | 210/198.2 |
| 4,758,340 | 7/1988 | Marchard | 210/198.2 |
| 4,792,396 | 12/1988 | Gundelfinger | 210/198.2 |
| 4,806,238 | 2/1989 | Sattler | 210/198.2 |
| 4,865,728 | 9/1989 | Larsson | 210/198.2 |
| 4,876,005 | 10/1989 | America | 210/198.2 |
| 4,888,112 | 12/1989 | Kronwald | 210/198.2 |
| 4,969,938 | 11/1990 | America | 96/105 |
| 5,169,522 | 12/1992 | Shalon | 210/198.2 |
| 5,188,730 | 2/1993 | Kronwald | 210/198.2 |
| 5,194,225 | 3/1993 | Muller | 210/198.2 |
| 5,227,059 | 7/1993 | Shepherd | 210/198.2 |
| 5,238,556 | 8/1993 | Shirkhan | 210/198.2 |

*Primary Examiner*—Ernest G. Therkorn
*Attorney, Agent, or Firm*—Andrew Alexander

[57] ABSTRACT

Disclosed is a cartridge for use in a chromatography system wherein fluid is introduced to and removed from the cartridge through a fluid connecting tube. The cartridge is comprised of a hollow tubular member suitable for containing sorbent material, the tubular member having at least a first hollow end portion. A plug member is provided inside the first hollow end portion suitable for containing the adsorbent material. The plug member has means for sealing the fluid tube in the cartridge and passing fluid to and from the sorbent.

22 Claims, 4 Drawing Sheets

CHROMATOGRAPHY CARTRIDGE

This application is a file wrapper continuation application of U.S. Ser. No. 08/157,469, filed Nov. 26, 1993, now abandoned.

BACKGROUND OF THE INVENTION

This invention relates to chromatography and more particularly, it relates to an improved cartridge column for use in a chromatography system.

Traditionally, columns or use in chromatography systems, including liquid, gas or supercritical fluid chromatography, usually employ a stainless steel tube in which is provided a packing material or sorbent. The sorbent is selected in accordance with the intended use and usually is held in the tube by use of a frit provided at both ends. Compression end fittings are used to hold the frit in place and to connect the column to an injector and to a detector. The compression end fittings normally employ nuts and ferrules on the outside of the column to close it. Nuts and ferrules are used to screw or join the column to the injector or detector by capillary tubing. The fittings at the ends of the column have to be provided with tapered seats on the end fittings in order to provide or a high compression seal on the column tube and connection tubing. However, the end fittings, ferrules, nuts and tapered seats employed add significantly to the cost and bulkiness of the column. Also, because of the design and relatively large ferrules employed and to provide a high compression seal, tools or wrenches often have to be used to tighten the nuts, making installation inconvenient.

Because of the problems with conventional columns, more recently cartridge columns have been employed. Cartridge columns do not require the bulky compression fittings. Thus, the overall cost of the column is reduced and ease of installation and use is improved. One type of cartridge column is disclosed in U.S. Pat. No. 4,283,280. In this design, the outside of the cartridge is smooth, and fritted seals are pressed onto each end to hold the packing material in place. However, this type of cartridge requires a special holder to fit over the cartridge which adds greatly to its expense and inconvenience. The holder is reusable but is limited in use to the same length cartridge, and the holder obscures the column label. Another type of cartridge column design employs threads on the outside of the cartridge column. This permits the reuse of the end fittings when the cartridge column is replaced. Also, most cartridge systems, especially for HPLC, are too bulky with special fittings or holders to fit into many types of popular block heaters, requiring larger air ovens for temperature control.

In yet another design, instead of threads, a groove is employed on the cartridge column. However, this design requires the use of a special collar and end fittings which add to the cost of the columns. Most of these cartridges require tools or extra parts such as holders for installation in a high pressure system for example, where leak-free operation is critical to function.

Thus, it will be seen that there is still a great need for an inexpensive, easy-to-install cartridge column for use in chromatographic systems at low or high pressures. The present invention provides such a cartridge column.

SUMMARY OF THE INVENTION

It is an object of the invention to provide an improved cartridge column for a chromatography system.

It is another object of the invention to provide a cartridge column that can be installed in a chromatography system and can be tightened without wrenches to sustain high system pressures.

It is yet another object of the invention to provide a cartridge column having an essentially smooth outer surface.

It is still yet another object of the invention to provide a cartridge column having means inside the column for sealing it to the chromatography system.

And yet it is another object of the invention to provide a cartridge column wherein threaded portions are provided inside or outside the column adjacent its end for purposes of fastening it in the chromatography system.

And yet it is another object of the invention to provide sealing means inside the cartridge column to retain packing or adsorbent material and to prevent escape of particles with the fluid flowing through the column.

In accordance with these objects, there is provided a cartridge for use in a chromatography system wherein fluid is introduced to and removed from the cartridge through a fluid connecting tube. The cartridge is comprised of a hollow tubular member, often containing sorbent material, the tubular member having a first hollow end portion and a second hollow end portion, each having an inside surface. A plug member is provided in at least one of the first hollow end portion and the second hollow end portion for containing sorbent material. The plug member also has means for sealing the fluid or connecting tube inside the cartridge for passing fluid through the tube.

DETAILED DESCRIPTION OF THE PREFERRED EMBODIMENTS OF THE INVENTION

Figure 1:
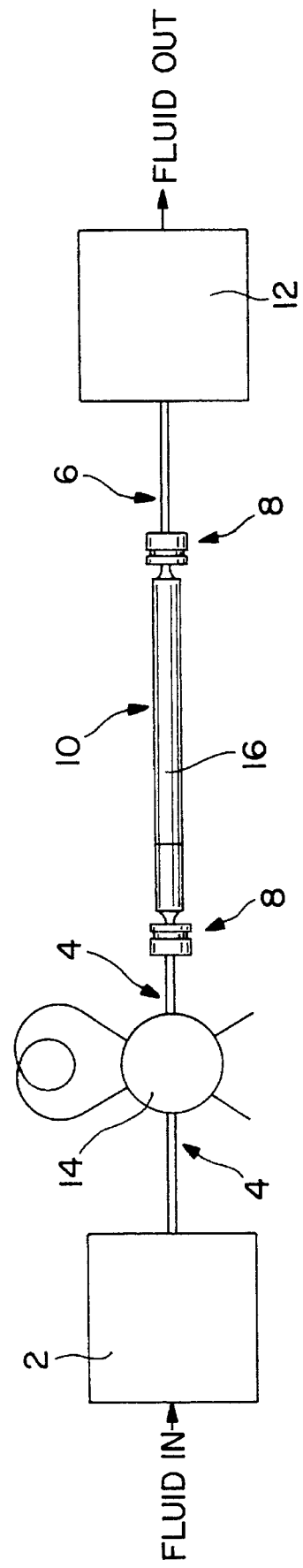
FIG. 1 is a schematic of a chromatography system including a high pressure pump, injector, cartridge column and detector in accordance with the invention.

Referring now to FIG. 1, there is shown a schematic example illustrating elements in a chromatography system including a high pressure pump 2 for supplying fluid at a high pressure as it is passed along tube 4 to cartridge column assembly 10 and then along tube 6 to detector 12. An injector 14 is provided to inject a sample into tube 4 to be analyzed or treated. Cartridge column assembly 10 comprises connector fittings 8 which are used to securely fasten tubes 4 and 6 to cartridge column 16 to provide a substantially leakproof connection. The novel cartridge column can be joined securely to the system without the use of tools to provide a leak-free connection that can withstand high internal pressures.

Figure 2:
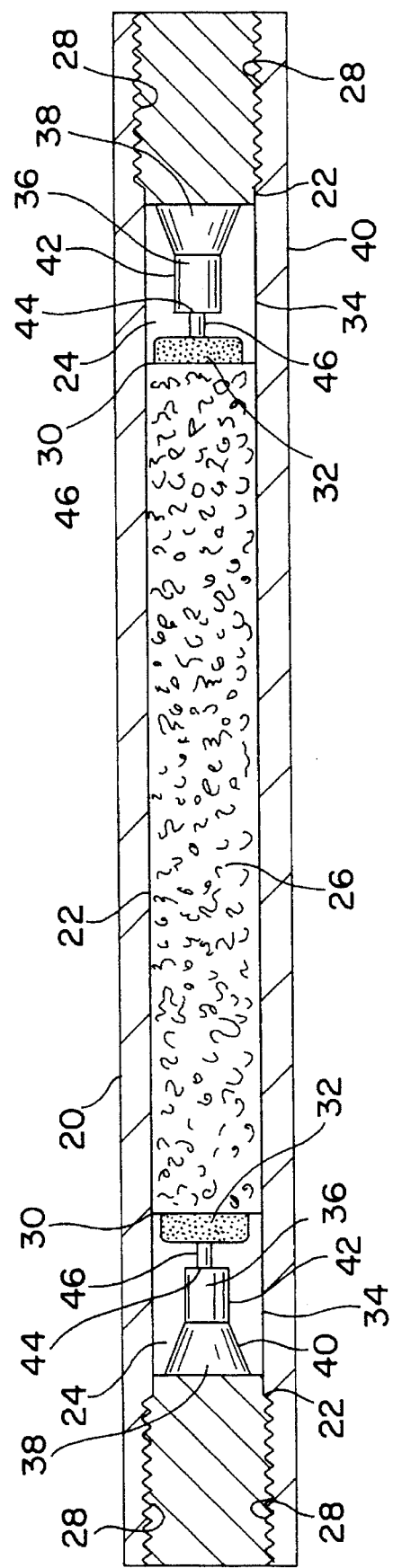
FIG. 2 is a cross section of a cartridge column of the invention.

In FIG. 2, there is shown a cross section of cartridge column 16 without connector fittings 8. Cartridge column 16 is comprised of a tubular member 20 that preferably has a cylindrical inside surface 22. Further, cartridge column 16 comprises plug members 24 that are utilized to provide a seal and to contain adsorbent or packing material 26. In addition, cartridge column 16 is provided with means, preferably inside threads 28, to securely fasten tubes 4 and 6 to the cartridge column. It will be appreciated that means for securing or fastening tubes 4 and 6 to cartridge column 16 can comprise a grooved end with a collar fitting or outside threads with suitable fittings. Preferably, tubular member 20 is provided with a stop or shoulder 30 in which plug member 24 can seat to prevent plug member 24 from sliding in the cartridge. Tubular member 20 can be comprised of metal, plastic, or other material of suitable strength. The preferred material for tubular member 20 is stainless steel.

Plug member 24 can be provided with a porous frit member 32 which serves to contain adsorbent or packing material 26 and to aid in dispersing fluid across the extent of packing material 26 for initial uniform contact therewith. Plug member 24 has a surface 34 for contacting inside surface 22 to form a seal therewith under cartridge column operating conditions. The seal is sufficient to prevent leakage of fluid, e.g., gas or liquid, when the column is operating under high pressure, for example 5,000 psi. Thus, plug member 24 has an outside surface 34 which fits the contour of inside surface 22 to provide a seal therebetween. Preferably, surface 34 of plug member 24 has a cylindrical configuration. Further, plug member 24 has a wall section 36 that defines an opening therethrough referred to generally as 38. Opening 38 has three sections. The first section has a surface 40 that converges inwardly and provides a seat for ferrule 50 surrounding tube 4 (see FIG. 3). Opening 38 has a second section or surface 42 that defines a cylindrical portion having a diameter about the same as the outside diameter of tube 4 and permits tube 4 to fit snugly thereinto. Second section 42 terminates in shoulder 44 that provides a stop for the end of tube 4. The third section of opening 38 is typically a narrow channel or conduit 46 which passes fluid from tube 4 to frit 32 and then into adsorbent 26.

As will be seen from FIG. 2, cartridge column 16 can be provided with a plug member 24 at each end. Further, plug member 24 can be removed from column 16 when the sorbent is spent, thus providing for inserting a new plug member. The description provided herein is suitable for either end, except, in one situation the fluid is being introduced to the column and at the opposite end fluid is being removed.

The frit disc is comprised of a porous material that will contain cartridge filling material such as adsorbent. Any material that is inert with respect to the fluids passing through the column may be used for the frit disc. Preferred materials from which the frit disc is fabricated comprise porous steel, titanium, plastic and the like.

From FIG. 2, it will be seen that plug member 24 has frit disc 32 contained, mounted or included therein. This helps ensure that fluid passes evenly through the frit disc and also provides for ease of assembly of the cartridge column. It will be understood that the frit disc can also be inserted in cartridge column 16 separate from plug member 24. That is, frit disc 32 can be placed adjacent the sorbent material and located between plug member 24, and sorbent material and frit disc 32 can extend to inside surface 22 to provide a layer between plug member 24 and sorbent material.

Figure 3:
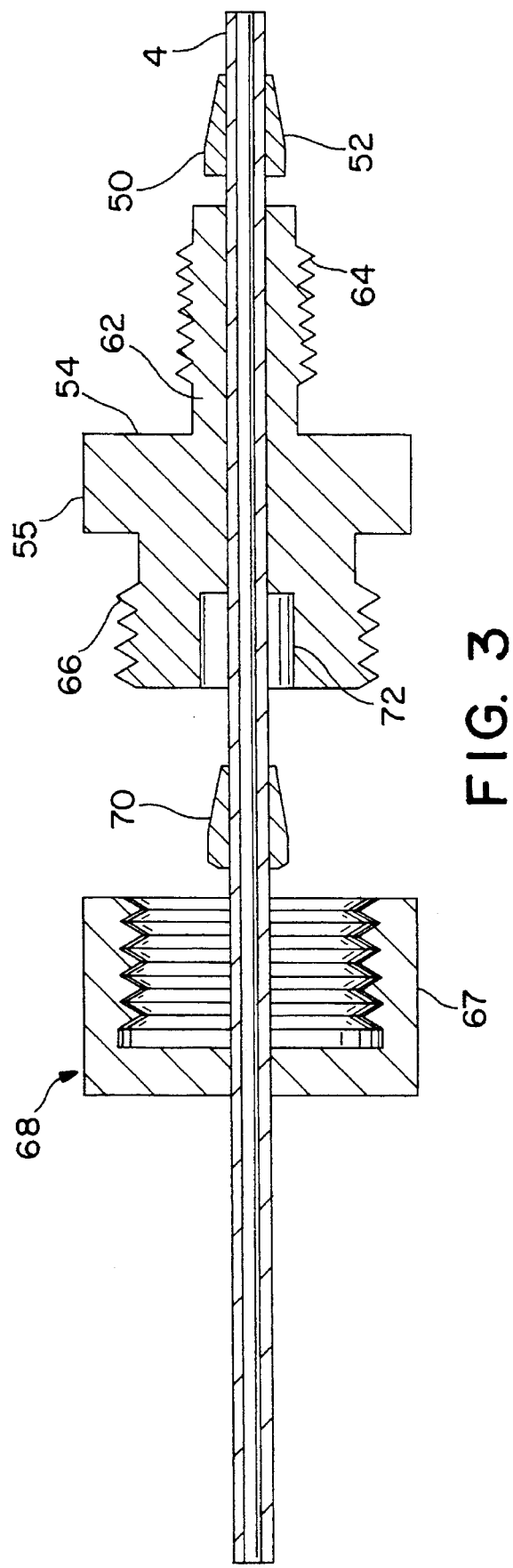
FIG. 3 is a cross section of a reusable connector fitting for fastening and sealing the connecting tube used for introducing to and removing fluid from the cartridge column.

In FIG. 3, there is shown a connector fitting assembly 60 which can be used at each end of cartridge column 16 to securely join and seal it into the chromatography system. Connector fitting assembly 60 is shown mounted on tube 4. Thus, connector fitting assembly 60 comprises a ferrule 50, threaded member 62 having a first threaded end 64 for threading into threads 28 of cartridge column 16 and a second threaded end 66 for threading into ferrule locking member 68. Between threaded member 62 and ferrule locking member 68 is provided ferrule 70 which is employed as a fixed flange. In the embodiment shown in FIG. 3, preferably ferrule 50 is a sealing ferrule and ferrule 70 is a locking flange ferrule. Further, it will be noted that ferrule 50, threaded member 62 and ferrule locking member 68 are slidably mounted on tube 4 prior to being fastened into cartridge column 16. Flange ferrule 70 is fastened on tube 4.

Figure 4:
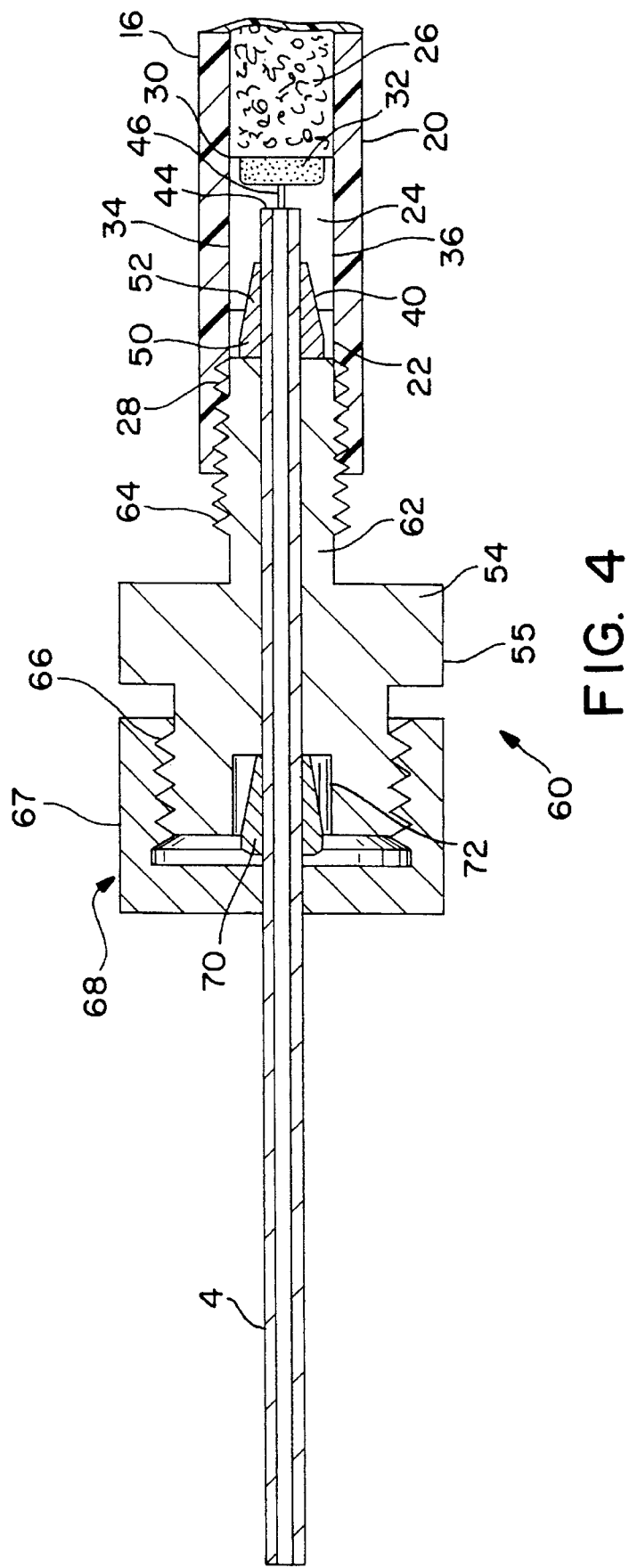
FIG. 4 is a cross-sectional view of the connector fittings and connecting tube fastened and sealed to one end of the cartridge column.

Sealing ferrule 50 is adapted to fit into plug member 24 and form a seal between surface 52 of ferrule 50 and surface 40 of plug member 24, as shown in FIG. 4. A circular extension 54, which may advantageously be provided with a knurled surface 55, is turned so as to thread connector fitting 62 into cartridge column 16 and provide torque. Ferrule 50 is forced against plug member surface 40 thereby sealing tube 4 into plug member 24. Further, plug member 24 is sealed against inside surface 22 of cartridge column 16. Thus, in installing cartridge column 16 in a chromatography system, tube 4 is placed in plug member 24 against shoulder 44 and end fitting 62 is then turned or screwed into threaded portion 28 to provide the desired seal with plug member 24. It will be understood that other sealing configurations inside a cartridge column can be used and such is contemplated within the purview of the subject invention.

In the present invention, it is preferred that plug member 24 be fabricated from a resilient material and that ferrule 50 be fabricated from a material having a hardness sufficient to form a seal, preferably without tools, as described. Further, preferably, it is important that the material comprising plug member 24 be inert with respect to fluid passing through cartridge column 16. Highly suitable materials to provide a non-metallic ferrule 50 include VESPEL® (DuPont), KEL-F® (3M), polyetheretherketone (PEEK), and other fluorocarbons or polymers. Materials that may be used to provide a non-metallic plug member 24 include nylon, polyethylene, polypropylene, polyetheretherketone, VESPEL®, or KEL-F®, for example. In certain cases, metals such as steel, copper, brass, aluminum and the like may be used for plug member or ferrule. It will be appreciated that ferrule 50 is comprised of a material sufficiently hard so as to effect a seal against plug member 24 which is sealed against surface 22. In a highly preferred embodiment, the materials for plug member 24 and ferrule 50 should be selected so that the material for the plug member is harder than that for ferrule 50 for purposes of prolonging the life of the plug member. Thus, it will be seen that the interaction of plug member 24 and ferrule 50 are important to permit reuse of ferrule 50 when the cartridge column is replaced. Further, because ferrule 50 is reused, it is important that it not bind on tube 4 so as to provide for slidable adjustments in fit when used with the next cartridge column or other conventional columns.

In this aspect of the invention, the sealing function of the cartridge column has been provided within the column. Also, the sealing function has been separated from fastening the cartridge column securely to the chromatography system. This is an important aspect of the invention because often it requires a different type of force to fasten the cartridge column into the chromatography system, particularly when operating at 5,000 psi, for example. Further, the forces for fastening tend to destroy seals for sealing and this is detrimental, particularly when it is attempted or desired to reuse seals many times.

For purposes of fastening tube 4 to cartridge column 16, a second fixed flange ferrule 70 is provided which fits into a stop 72 in connector fitting 62. Second ferrule 70 is locked or crimped or securely attached to tube 4 to act only as a fixed flange. Also, connector fitting 62 is provided with threads 66 so that locking ferrule member 68 can be threaded thereon, thereby providing a mechanical fastening means to adjustably hold tube 4 in plug member 24. The action of pushing down on flange ferrule 70 by locking member 68 forces tube 4 to make a snug fit in plug 24 which minimizes harmful gaps or voids occurring during installation and operation. The length of threads 66 and 67 permit for adjustments with respect to location of plug member 24 in cartridge column 16 and yet means have been provided for securely fastening tube 4 into cartridge column 16 and insuring a good fit. While threads 64 are shown in their most common configuration on the outside surface of connector fitting 62, such threads can be provided on an inside surface to accommodate threads on an outside surface of the cartridge column. Also, other such changes may be made, all of which are contemplated within the purview of the invention.

It will be appreciated that flange ferrule 70 does not have to seal forcibly into stop 72 to provide a seal and thus it can be reused many times without fear of deforming tube 4, ferrule 70 or stop 72. In addition, the cartridge column and system has the advantage that it can be used in different lengths without the need for expensive holders.

While the invention has been described in reference to a chromatography system, it will be appreciated that its use is not necessarily limited thereto. That is, the invention can be used for any type of trapping or filtration of particles. For example, a short cartridge without sorbent can be used as an inexpensive or disposable filter for a particle trap wherein frit disc 32 is used as a filter. Various frit disc diameters can be used in the same diameter cartridge to provide optimum filtration for various flow rates in different diameter columns. Further, the invention can be used with or without sorbent contained in the tube. Also, the cartridge may be designed to utilize plug member 24 in one end only. If required, the other end may utilize a conventional fitting. Thus, the invention may be used in any type of column, including but not limited to analytical, guard, trap, HPLC, GC, packed end open tube capillary GC, SFC or other types of columns. In addition, the invention can be used in large or small diameter columns with an adapter utilized in the large diameter, if necessary. By use of the present invention, a standard thread diameter can be used with different inside diameter cartridges, and only the geometry of the plug member needs to be changed. This greatly minimizes the number of end fittings required. Further, plug member 24 may be used in the above said adapter attached to the cartridge. When plug member 24 is utilized in an adapter attached to a cartridge, for purposes of the present invention this is considered to come within the meaning of the word cartridge as used herein.

While the invention has been described in terms of preferred embodiments, the claims appended hereto are intended to encompass other embodiments which fall within the spirit of the invention.

What is claimed is:

1. A cartridge for use in a chromatography system wherein fluid is introduced to and removed from said cartridge through a fluid connecting tube, said cartridge consisting essentially of:
   (a) a hollow metal tubular member suitable for containing sorbent material, said tubular member having a first hollow end portion and a second hollow end portion each having an inside surface;
   (b) a plug member provided in at least one of said first hollow end portion and said second hollow end portion in non-sliding contact therewith, said plug member having means for providing a seal against said inside surface of the hollow end portion of said cartridge and said plug member also having means for sealing said fluid connecting tube in said cartridge and means for passing fluid through said tubular member; and
   (c) means separate from said sealing means for fastening said fluid connecting tube in said cartridge comprising a threaded portion provided inside said hollow end portion.

2. The cartridge in accordance with claim 1 wherein said plug member has a frit plate associated wherewith to disperse fluid introduced to said absorbent.

3. The cartridge in accordance with claim 1 wherein said plug member comprises:
   (a) means for providing a seal against said inside surface;
   (b) means for providing a seal with a ferrule on said fluid connecting tube; and
   (c) an opening therethrough for passing said fluid from said fluid connecting tube to or from said sorbent material.

4. The cartridge in accordance with claim 3 wherein said plug member and said ferrule are comprised of a non-metallic material.

5. The cartridge in accordance with claim 1 wherein the plug member is comprised of:
   (a) a wall having an outer surface and an inner surface, said outer surface adapted for sealing against said inside surface of said end portion; and
   (b) a first end and a second end connected by said wall:
      (i) said first end positioned adjacent sorbent material; and
      (ii) said wall inner surface defining:
         a cone-shaped portion that tapers inwardly from said second end towards said first end; and
         a cylindrical portion for receiving said fluid connecting tube, the cylindrical portion extending from said cone-shaped portion toward said first end, said cylindrical portion terminating in a shoulder having an opening therein for passing fluid to or from said adsorbent material.

6. The cartridge in accordance with claim 5 wherein a ferrule is positioned on said tube to effect a seal between said cone-shaped surface and said ferrule and between said plug wall outer surface and said inside surface of said hollow tubular member.

7. The cartridge in accordance with claim 6 wherein said ferrule is comprised of a non-metallic material.

8. The cartridge in accordance with claim 5 wherein said first end has a frit plate associated therewith.

9. The cartridge in accordance with claim 1 wherein said plug member is fabricated from a non-metallic material substantially inert to said fluid.

10. A cartridge for use in a chromatography system wherein fluid is introduced to and removed from said cartridge through a fluid connecting tube, said cartridge consisting essentially of:
   (a) a hollow metal tubular member containing sorbent material, said tubular member having a first end portion and a second end portion each having an inside surface;
   (b) a plug member provided in said first end portion and said second end portion, said plug member comprised of:
      (i) means for providing a seal against said inside surface;
      (ii) means for providing a seal with a ferrule on said fluid connecting tube; and
      (iii) an opening therethrough for passing said fluid from said fluid connecting tube to or from said sorbent material; and
   (c) means separate from said sealing means for fastening said fluid connecting tube in said cartridge comprising a threaded portion provided inside said hollow end portion.

11. The cartridge in accordance with claim 10 wherein said plug member has a frit plate associated therewith for containing said sorbent.

12. The cartridge in accordance with claim 10 wherein said plug member is comprised of a non-metallic material having a hardness greater than the hardness of a non-metallic material comprising said ferrule.

13. The cartridge in accordance with claim 10 wherein the plug member is comprised of:
    (a) a wall having an outer surface and an inner surface, said outer surface adapted for sealing against said inside surface of said end portion;
    (b) a first end and a second end connected by said wall
        (i) said first end positioned adjacent said sorbent material; and
        (ii) said wall inner surface defining:
            a cone-shaped portion that tapers inwardly from said second end towards said first end; and
            a cylindrical portion for receiving said fluid connecting tube, the cylindrical portion extending from said cone-shaped portion toward said first end, said cylindrical portion terminating in a shoulder having an opening therein for passing fluid to or from said sorbent material.

14. The cartridge in accordance with claim 13 wherein said ferrule is forced against said plug member by a threaded member slidably mounted on said fluid connecting tube, the threaded member having a first section thereof having first threads suited for engaging threads on said cartridge and adapted to press said ferrule against said plug member for purposes of sealing said tube in said cartridge.

15. The cartridge in accordance with claim 14 wherein said threaded member has a second section having second threads thereon and a ferrule stop.

16. A cartridge for use in a chromatography system wherein fluid is introduced to and removed from said cartridge through a fluid connection tube, said cartridge consisting essentially of:
    (a) a hollow metal tubular member suitable for containing sorbent material, said tubular member having a first hollow end portion and a second hollow end portion each having a cylindrical inside surface; and
    (b) a plug member provided inside said first hollow end portion and said second hollow end portion for containing said sorbent material, the plug member comprised of:
        (i) a wall having an outer surface and an inner surface, said outer surface adapted for sealing against said inside surface of said end portion;
        (ii) a first end and a second end connected by said wall
        (iii) said first end positioned adjacent said adsorbent material; and
        (iv) said wall inner surface defining:
            a cone-shaped portion that tapers inwardly from said second end towards said first end and adapted to provide a seal with a ferrule positioned on said fluid connection tube; and
            a cylindrical portion for receiving said fluid connecting tube, the cylindrical portion extending from said cone-shaped portion toward said first end, said cylindrical portion terminating in a shoulder having an opening therein for passing fluid to or from said adsorbent material; and
    (c) means separate from said sealing means for fastening said fluid connecting tube in said cartridge comprising a threaded portion provided inside said hollow end portion.

17. The cartridge in accordance with claim 16 wherein a frit plate is positioned between said first end and sorbent material.

18. The cartridge in accordance with claim 17 wherein said fluid connecting tube has a second ferrule fixedly attached thereto and a threaded lock member slidably mounted on said fluid connecting tube, the threaded lock member adapted to engage said second threads on said threaded member for forcing said second ferrule against said ferrule stop on said threaded member thereby fastening said fluid connecting tube to said threaded member to prevent withdrawal.

19. The cartridge in accordance with claim 16 wherein said plug member is comprised of a material having a hardness greater than the hardness of a material comprising said ferrule.

20. The cartridge in accordance with claim 16 wherein said plug member is comprised of a material having a hardness less than the hardness of a material comprising said ferrule.

21. The cartridge in accordance with claim 10 or 16 wherein said means for sealing comprises a first ferrule slidably mounted on said fluid connecting tube adapted to be forced against said plug member for purposes of sealing said fluid tube in said cartridge.

22. A cartridge for use in a chromatography system wherein fluid is introduced to and removed from said cartridge through a fluid connecting tube, said cartridge consisting essentially of:
    (a) a hollow metal tubular member suitable for containing sorbent material, said tubular member having a first hollow end portion and a second hollow end portion each having an inside surface;
    (b) a plug member provided in at least one of said first hollow end portion and said second hollow end portion in non-sliding contact therewith, said plug member having means for providing a seal against said inside surface of the hollow end portion of said cartridge and means for sealing said fluid connecting tube in said cartridge comprising a first ferrule adapted to be forced against said plug member by a threaded member slidably mounted on said fluid connecting tube, the threaded member having a first section thereof having first threads thereon for engaging inside threads in at least one of said hollow end portions, said threaded member adapted to press said first ferrule against said plug member for purposes of sealing said tube in said hollow tubular member and for passing fluid through said tubular member;
    (c) means for fastening said fluid connecting tube in said cartridge comprising a threaded portion provided inside said hollow end portion for receiving said first threads; and
    (d) a second ferrule fixedly attached to said connecting tube and a threaded lock member slidably mounted on said fluid connecting tube, said threaded lock member adapted to engage said second threads on said threaded member for forcing said second ferrule against said thread member thereby fastening said fluid connecting tube to said hollow tubular member.

* * * * *